(12) United States Patent
Sakanishi et al.

(10) Patent No.: US 10,011,561 B2
(45) Date of Patent: *Jul. 3, 2018

(54) THICKENING/STABILIZING AGENT AND THICKENED/STABILIZED COMPOSITION USING THE SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Ohtake (JP); Takashi Saeki, Ube (JP); Mami Itoh, Ube (JP)

(73) Assignees: DAICEL CORPORATION, Osaka-Shi (JP); YAMAGUCHI UNIVERSITY, Yamaguchi-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/323,627

(22) PCT Filed: Jul. 7, 2015

(86) PCT No.: PCT/JP2015/069478
§ 371 (c)(1),
(2) Date: Jan. 3, 2017

(87) PCT Pub. No.: WO2016/006590
PCT Pub. Date: Jan. 14, 2016

(65) Prior Publication Data
US 2017/0137373 A1    May 18, 2017

(30) Foreign Application Priority Data

Jul. 7, 2014   (JP) .................................. 2014-139534

(51) Int. Cl.
| | | |
|---|---|---|
| *C07C 235/84* | (2006.01) | |
| *C07C 235/82* | (2006.01) | |
| *A61K 8/42* | (2006.01) | |
| *A61K 47/18* | (2017.01) | |
| *A23L 29/20* | (2016.01) | |
| *C09D 7/00* | (2018.01) | |
| *C09D 7/43* | (2018.01) | |

(52) U.S. Cl.
CPC ............ *C07C 235/84* (2013.01); *A23L 29/20* (2016.08); *A61K 8/42* (2013.01); *A61K 47/18* (2013.01); *C07C 235/82* (2013.01); *C09D 7/002* (2013.01); *C09D 7/43* (2018.01); *A23V 2002/00* (2013.01); *A61K 2800/10* (2013.01); *A61K 2800/48* (2013.01)

(58) Field of Classification Search
CPC ...... C07C 235/84; C07C 235/82; C09D 7/002
See application file for complete search history.

(56) References Cited

U.S. PATENT DOCUMENTS

| | | | |
|---|---|---|---|
| 2013/0085087 A1 | 4/2013 | Mesher et al. | |
| 2014/0142004 A1 | 5/2014 | Mesher et al. | |
| 2015/0376119 A1 | 12/2015 | Sakanishi et al. | |
| 2016/0310384 A1 | 10/2016 | Sakanishi et al. | |

FOREIGN PATENT DOCUMENTS

| | | | |
|---|---|---|---|
| JP | 1-163111 A | 6/1989 | |
| JP | 7-325431 A | 12/1995 | |
| JP | 2012-77195 A | 4/2012 | |
| JP | 2012077195 A * | 4/2012 | |
| WO | WO 2013/040718 A1 | 3/2013 | |
| WO | WO-2013040718 A1 * | 3/2013 | ............ C09K 8/035 |
| WO | WO 2014/123110 A1 | 8/2014 | |
| WO | WO 2014/208380 A1 | 12/2014 | |
| WO | WO 2015/029764 A1 | 3/2015 | |
| WO | WO 2015/083740 A1 | 6/2015 | |
| WO | WO 2015/087811 A1 | 6/2015 | |

OTHER PUBLICATIONS

U.S. Appl. No. 15/310,146, filed Nov. 2016, Sakanishi et al.*
International Search Report issued in PCT/JP2015/069478 (PCT/ISA/210), dated Sep. 29, 2015.
Written Opinion of the International Searching Authority issued in PCT/JP2015/069478 (PCT/ISA/237), dated Sep. 29, 2015.

* cited by examiner

*Primary Examiner* — Amanda L Aguirre
(74) *Attorney, Agent, or Firm* — Birch, Stewart, Kolasch & Birch, LLP

(57) ABSTRACT

A compound that thickens and/or gelatinizes a fluid organic substance to a desired viscosity, or uniformly stabilizes a composition containing the fluid organic substance. Also, a thickening/stabilizing agent including the compound, a thickened/stabilized composition including the thickening/stabilizing agent and a fluid organic substance, and a method for producing the composition. The compound according to the present invention is represented by Formula (1):

$$(R^2-HNOC)_{4-n}-R^1-(CONH-R^3)_n \qquad (1)$$

where $R^1$ is a group resulting from removing four hydrogen atoms from the structural formula of an aromatic hydrocarbon or cyclohexane, $R^2$ is, independently in each occurrence, an aliphatic hydrocarbon group containing 1 to 4 carbon atoms, $R^3$ is, independently in each occurrence, an aliphatic hydrocarbon group containing 6 or more carbon atoms, and n is an integer of 1 to 3.

6 Claims, No Drawings

THICKENING/STABILIZING AGENT AND THICKENED/STABILIZED COMPOSITION USING THE SAME

TECHNICAL FIELD

The present invention relates to a novel compound that has the activity of thickening/stabilizing oils and other fluid organic substances. The present invention also relates to a thickening/stabilizing agent including the compound; and to a thickened/stabilized composition containing the thickening/stabilizing agent. The present application claims priority to Japanese Patent Application No. 2014-139534 filed to Japan on Jul. 7, 2014, the entire contents of which are incorporated herein by reference.

BACKGROUND ART

Techniques for thickening/stabilizing liquids are industrially very important. For example, mayonnaise and salad dressing, which are emulsions in metastable states, can stably maintain their emulsified states over the long term because their aqueous components are thickened/stabilized. For the thickening/stabilizing techniques, a variety of thickening/stabilizing agents have been developed. For example, alkyl acrylate copolymers are known as thickening/stabilizing agents for aqueous media (aqueous vehicles).

In contrast, 12-hydroxystearic acid is known as a thickening/stabilizing agent for fluid organic substances (such as oily media and other organic substances having fluidity) (Patent Literature (PTL) 1), where 12-hydroxystearic acid is mainly used for waste disposal of edible oils. However, 12-hydroxystearic acid is does not permit adjustment of the degree of gelatinization that it imparts, and can only cause the target component to be brought into a completely solidified state or to remain in a liquid state.

CITATION LIST

Patent Literature

PTL 1: Japanese Unexamined Patent Application Publication (JP-A) No. H01-163111

SUMMARY OF INVENTION

Technical Problem

Accordingly, the present invention has an object to provide a compound that thickens or gelatinizes a fluid organic substance to a desired viscosity, or uniformly stabilizes a composition containing the fluid organic substance.

The present invention has another object to provide a thickening/stabilizing agent containing the compound, a thickened/stabilized composition which is thickened, gelatinized, or stabilized by the thickening/stabilizing agent, and a method for producing the thickened/stabilized composition.

Solution to Problem

After intensive investigations to achieve the objects, the inventors of the present invention found compounds having a specific structure and found that the compounds thicken and/or gelatinize a fluid organic substance, or uniformly stabilize a composition containing the fluid organic substance, namely, the compounds eliminate or minimize sedimentation, local aggregation, and concentration of the composition and can maintain the uniform state of the composition. The inventors also found that, when a compound is selected, from among the compounds, according to the type of a fluid organic substance, the compound can thicken and/or gelatinize the fluid organic substance to a desired viscosity, or can uniformly stabilize a composition containing the fluid organic substance. The present invention has been made on the basis of these findings.

Specifically, the present invention provides, in an aspect, a compound represented by Formula (1):

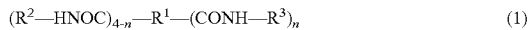

$$(R^2-HNOC)_{4-n}-R^1-(CONH-R^3)_n \qquad (1)$$

where $R^1$ is a group resulting from removing four hydrogen atoms from the structural formula of an aromatic hydrocarbon or cyclohexane; $R^2$ is, independently in each occurrence, an aliphatic hydrocarbon group containing 1 to 4 carbon atoms; $R^3$ is, independently in each occurrence, an aliphatic hydrocarbon group containing 6 or more carbon atoms; and n is an integer of 1 to 3.

In the compound, the aromatic hydrocarbon in $R^1$ may be selected from benzene, benzophenone, biphenyl, and naphthalene.

In the compound, $R^1$ may be a group resulting from removing four hydrogen atoms from the structural formula of one of benzene and cyclohexane.

The present invention provides, in another aspect, a thickening/stabilizing agent including the compound.

The present invention provides, in yet another aspect, a thickened/stabilized composition including the thickening/stabilizing agent and a fluid organic substance.

The present invention provides, in still another aspect, a method for producing a thickened/stabilized composition. The method includes the step of dissolving the thickening/stabilizing agent and a fluid organic substance mutually in each other.

Specifically, the present invention relates to followings.

(1) The present invention relates to a compound represented by Formula (1):

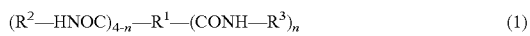

$$(R^2-HNOC)_{4-n}-R^1-(CONH-R^3)_n \qquad (1)$$

where $R^1$ is a group resulting from removing four hydrogen atoms from the structural formula of an aromatic hydrocarbon or cyclohexane; $R^2$ is, independently in each occurrence, an aliphatic hydrocarbon group containing 1 to 4 carbon atoms; $R^3$ is, independently in each occurrence, an aliphatic hydrocarbon group containing 6 or more carbon atoms; and n is an integer of 1 to 3.

(2) In the compound according to (1), the aromatic hydrocarbon in $R^1$ may be selected from benzene, benzophenone, biphenyl, and naphthalene.

(3) In the compound according to (1), $R^1$ may be a group resulting from removing four hydrogen atoms from the structural formula of one of benzene and cyclohexane.

(4) In the compound according to any one of (1) to (3), the aliphatic hydrocarbon group as $R^2$ may be, independently in each occurrence, selected from linear or branched alkyl, linear or branched alkenyl, and linear or branched alkynyl.

(5) In the compound according to any one of (1) to (4), $R^3$ may be, independently in each occurrence, selected from $C_6$ or higher linear or branched alkyl and $C_6$ or higher linear or branched alkenyl.

(6) In the compound according to any one of (1) to (4), $R^3$ may be, independently in each occurrence, selected from $C_6$-$C_{20}$ linear or branched alkyl and $C_6$-$C_{20}$ linear or branched alkenyl.

(7) The compound according to (1) may be at least one compound selected from the group consisting of compounds represented by Formulae (1-1) to (1-22).

(8) The compound according to (1) may be at least one compound selected from the group consisting of compounds represented by Formulae (1-1) to (1-4) and (1-19) to (1-22).

(9) The compound according to (1) may be at least one of the compound represented by Formula (1-2) and the compound represented by Formula (1-4) and/or at least one of the compound represented by Formula (1-20) and the compound represented by Formula (1-22).

(10) The present invention also relates to a thickening/stabilizing agent including the compound according to any one of (1) to (9).

(11) In the thickening/stabilizing agent according to (10), the compound represented by Formula (1) may be present in a content of 0.5 weight percent or more of the total weight of the thickening/stabilizing agent, where, when two or more different compounds represented by Formula (1) are present, the term "content" refers to the total content of them.

(12) The present invention also relates to a thickened/stabilized composition including the thickening/stabilizing agent according to one of (10) and (11), and a fluid organic substance.

(13) In the thickened/stabilized composition according to (12), the fluid organic substance may have a viscosity (viscosity ($\eta$) at 25° C. and a shear rate of 10 (1/s)) of less than 0.1 Pa·s as determined using a rheometer.

(14) In the thickened/stabilized composition according to one of (12) and (13), the fluid organic substance may be at least one compound selected from the group consisting of hydrocarbon oils, ethers, halogenated hydrocarbons, petroleum components, animal and vegetable oils, silicone oils, esters, aromatic carboxylic acids, and pyridine.

(15) In the thickened/stabilized composition according to any one of (12) to (14), the thickening/stabilizing agent may be present in a proportion of 0.1 to 100 parts by weight per 1000 parts by weight of the fluid organic substance.

(16) The present invention also relates to a method for producing a thickened/stabilized composition. The method includes the step of dissolving the thickening/stabilizing agent according to one of (10) and (11) and a fluid organic substance mutually in each other.

(17) The present invention also relates to a method for producing a thickened/stabilized composition. The method includes the step of dissolving the thickening/stabilizing agent according to one of (10) and (11) and a fluid organic substance mutually in each other, to form the thickened/stabilized composition according to any one of (12) to (15).

Advantageous Effects of Invention

The compound represented by Formula (1) according to the present invention, when mutually dissolved in a fluid organic substance, can readily thicken and/or gelatinize the fluid organic substance, or can uniformly stabilize a composition containing the fluid organic substance. In addition, a compound thickened/stabilized by the compound represented by Formula (1) according to the present invention can maintain its thickened and/or stabilized state stably. Thus, the compound represented by Formula (1) according to the present invention is advantageously usable as thickening/stabilizing agents typically for cosmetics, coating materials, foodstuffs, and pharmaceutical preparations. The compound represented by Formula (1) according to the present invention, when used, allows these substances or materials to have viscosities adjusted within desired ranges and to maintain their formulations (compositions) uniformly, to offer better usability.

DESCRIPTION OF EMBODIMENTS

Compounds Represented by Formula (1)

The compounds according to the present invention are represented by Formula (1):

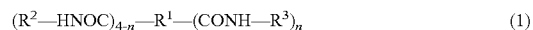

$$(R^2\text{—HNOC})_{4-n}\text{—}R^1\text{—}(\text{CONH—}R^3)_n \qquad (1)$$

In the formula, $R^1$ is a group resulting from removing four hydrogen atoms from the structural formula of an aromatic hydrocarbon or cyclohexane; $R^2$ is, independently in each occurrence, an aliphatic hydrocarbon group containing 1 to 4 carbon atoms; $R^3$ is, independently in each occurrence, an aliphatic hydrocarbon group containing 6 or more carbon atoms; and n is an integer of 1 to 3.

Non-limiting examples of the aromatic hydrocarbon in $R^1$ include $C_6$-$C_{14}$ aromatic rings such as benzene and naphthalene rings; and structures each including two or more of the aromatic rings bonded to each other through a single bond or a linkage group.

Non-limiting examples of the linkage group include divalent hydrocarbon groups, carbonyl (—CO—), ether bond (—O—), thioether bond (—S—), ester bond (—COO—), amido bond (—CONH—), carbonate bond (—OCOO—), and groups each including two or more of these groups linked to each other.

Non-limiting examples of the divalent hydrocarbon groups include $C_1$-$C_{18}$ linear or branched alkylene such as methylene, methylmethylene, dimethylmethylene, ethylene, propylene, and trimethylene; and $C_3$-$C_{18}$ cycloalkylene (including cycloalkylidene), such as 1,2-cyclopentylene, 1,3-cyclopentylene, cyclopentylidene, 1,2-cyclohexylene, 1,3-cyclohexylene, 1,4-cyclohexylene, and cyclohexylidene.

In particular, the aromatic hydrocarbon in $R^1$ is preferably selected from benzene, benzophenone, biphenyl, and naphthalene, and is particularly preferably benzene. Accordingly, $R^1$ herein is preferably a group resulting from removing four hydrogen atoms from the structural formula of one of benzene and cyclohexane.

$R^2$ is, independently in each occurrence, an aliphatic hydrocarbon group containing 1 to 4 carbon atoms and is exemplified by, but not limited to, linear or branched alkyl such as methyl, ethyl, n-propyl, isopropyl, n-butyl, s-butyl, and t-butyl; linear or branched alkenyl such as ethenyl, propenyl, and butenyl; and linear or branched alkynyl such as ethynyl, propynyl, and butynyl.

Non-limiting examples of the aliphatic hydrocarbon group containing 6 or more carbon atoms, as $R^3$, include linear or branched alkyl containing 6 to about 20 carbon atoms, such as hexyl, octyl, 2-ethylhexyl, decyl, lauryl, myristyl, stearyl, and nonadecyl, of which one containing 6 to 18 carbon atoms is preferred; linear or branched alkenyl containing 6 to about 20 carbon atoms, such as 2-hexenyl, 3-hexenyl, 4-hexenyl, 5-hexenyl, 7-octenyl, 9-decenyl, 11-dodecenyl, and oleyl, of which one containing 6 to 18 carbon atoms is preferred; and linear or branched alkynyl containing 6 to about 20 carbon atoms, such as hexynyl, octynyl, decynyl, pentadecynyl, and octadecynyl, of which one containing 6 to 18 carbon atoms is preferred, and one containing 12 to 18 carbon atoms is particularly preferred. Among them, the aliphatic hydrocarbon group containing 6 or more carbon atoms herein is preferably selected from $C_6$ or higher linear or branched alkyl and $C_6$ or higher linear or branched alkenyl and is particularly preferably selected from $C_6$-$C_{20}$ linear or branched alkyl and $C_6$-$C_{20}$ linear or branched alkenyl.
Non-limiting examples of the compounds represented by Formula (1) include compounds represented by the formulae:
[Chem. 1]
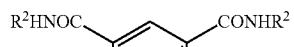
(1-1)
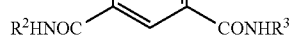
(1-2)
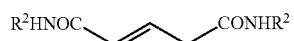
(1-3)
(1-4)
[Chem. 2]
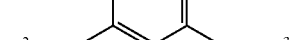
(1-5)
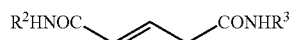
(1-6)
(1-7)
(1-8)
(1-9)
-continued
[Chem. 3]
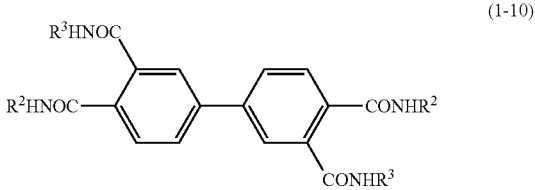
(1-10)
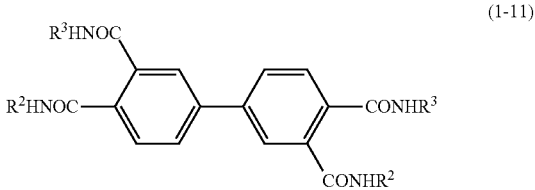
(1-11)
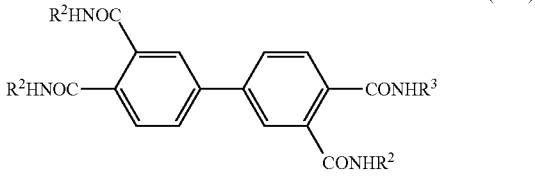
(1-12)
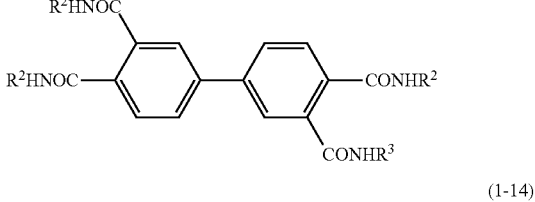
(1-13)
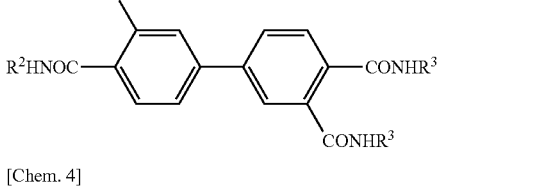
(1-14)
[Chem. 4]
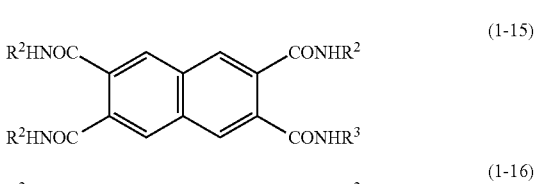
(1-15)
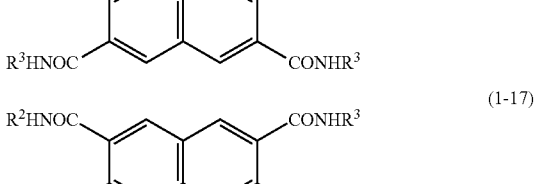
(1-16)
(1-17)
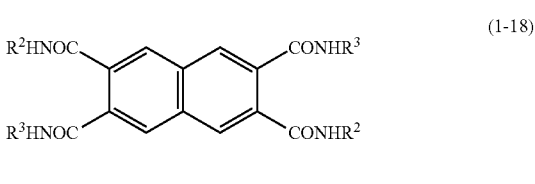
(1-18)

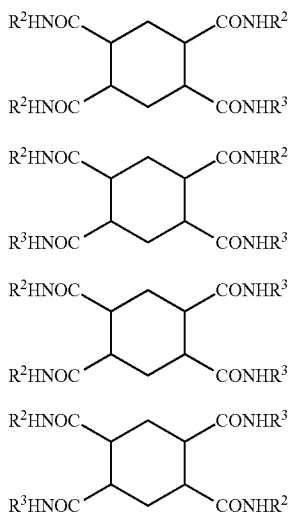

Among the compounds represented by Formula (1), the compounds represented by Formulae (1-1) to (1-4) and (1-19) to (1-22) are preferred. These compounds are preferred because they have excellent solubility in a fluid organic substance, and can impart pseudoplasticity behavior and high storage modulus to the fluid organic substance while maintaining its transparency when the fluid organic substance is transparent. In particular, at least one of the compound represented by Formula (1-2) and the compound represented by Formula (1-4); and at least one of the compound represented by Formula (1-20) and the compound represented by Formula (1-22) are preferred.

The compounds represented by Formula (1) can each be produced typically by methods 1 and 2 as follows.

In the method 1, a carboxylic acid ($R^1$—$(COOH)_4$, where $R^1$ is as defined above) is reacted with thionyl chloride to give a carboxylic acid chloride, and the resulting carboxylic acid chloride is reacted with amines ($R^2$—$NH_2$ and $R^3$—$NH_2$, where $R^2$ and $R^3$ are as defined above).

In the method 2, a carboxylic anhydride corresponding to the carboxylic acid is reacted with an amine (1) ($R^2$—$NH_2$ or $R^3$—$NH_2$, where $R^2$ and $R^3$ are as defined above) to give an amic acid, and the amic acid is further condensed with an amine (2) using a condensing agent. Herein, when the amine (1) is $R^2$—$NH_2$, the amine (2) is $R^3$—$NH_2$; and when the amine (1) is $R^3$—$NH_2$, the amine (2) is $R^2$—$NH_2$, where $R^2$ and $R^3$ are as defined above.

Specifically, non-limiting examples of the carboxylic acid for use in the method 1 include 1,2,4,5-benzenetetracarboxylic acid, 3,3',4,4'-benzophenonetetracarboxylic acid, 1,1'-biphenyl-2,3,3',4'-tetracarboxylic acid, 1,4,5,8-naphthalenetetracarboxylic acid, and 1,2,4,5-cyclohexanetetracarboxylic acid.

Non-limiting examples of the amine $R^2$—$NH_2$ for use in the method 1 include methylamine, ethylamine, n-propylamine, isopropylamine, n-butylamine, s-butylamine, and t-butylamine.

Non-limiting examples of the amine $R^3$—$NH_2$ for use in the method 1 include amines in which $R^3$ is an aliphatic hydrocarbon group (preferably, linear or branched alkyl, alkenyl, or alkynyl) containing 6 or more (preferably 6 to 20) carbon atoms, such as hexylamine, octylamine, 2-ethylhexylamine, decylamine, laurylamine, myristylamine, stearylamine, and oleylamine.

The reaction between the carboxylic acid chloride and the amines in the method 1 may be performed typically by adding the carboxylic acid chloride dropwise to a system containing the amines.

The amines may be used in an amount (a total amount of $R^2$—$NH_2$ and $R^3$—$NH_2$) of typically about 3 to about 8 moles, and preferably 3 to 6 moles, per mole of the carboxylic acid chloride. The adjustment of the proportions of $R^2$—$NH_2$ and $R^3$—$NH_2$ to be used can control the numbers of (CONH—$R^2$) group or groups and (CONH—$R^3$) group or groups in each compound represented by Formula (1).

The reaction between the carboxylic acid chloride and the amines may be performed in the presence of, or in the absence of, a solvent. Non-limiting examples of the solvent include saturated or unsaturated hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentylmethyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of them may be used alone or in combination as a mixture.

The solvent may be used in an amount of typically about 50 to about 300 weight percent, and preferably 100 to 250 weight percent, relative to the total weight of the carboxylic acid chloride and the amines. The solvent, when used in an amount greater than the range, tends to cause a lower reaction rate because of lower concentration of reactants (reaction components).

The reaction (via dropping) between the carboxylic acid chloride and the amines is generally performed at normal atmospheric pressure. The reaction atmosphere (i.e., dropping atmosphere) is not limited, as long as not adversely affecting the reaction, and may be selected from any atmospheres such as air atmosphere, nitrogen atmosphere, and argon atmosphere. The reaction may be performed at a reaction temperature (i.e., temperature upon dropping) of typically about 30° C. to 60° C. for a reaction time (i.e., dropping time) of typically about 0.5 to about 20 hours. The method may further include an aging step after the completion of the reaction (i.e., after the completion of dropping). When the method includes the aging step, the aging may be performed at a temperature of typically about typically about 30° C. to about 60° C. for a time of typically about 1 to about 5 hours. The reaction may be performed according to any system such as batch system, semi-batch system, or continuous system.

After the completion of the reaction, the resulting reaction product may be separated/purified typically by a separation process such as filtration, concentration, distillation, extraction, crystallization, adsorption, recrystallization, or column chromatography, or a separation process as any combination of them.

According to the production method 2, each compound represented by Formula (1) may be produced typically by charging the carboxylic anhydride, the amine (1), and a solvent mentioned below into a system, aging the components to give an amic acid, and then charging the amine (2) and the condensing agent (such as a carbodiimide or a salt thereof), followed by aging.

Non-limiting examples of the carboxylic anhydride for use in the method 2 include 1,2,4,5-benzenetetracarboxylic 1,2:4,5-dianhydride, 3,3',4,4'-benzophenonetetracarboxylic dianhydride, 1,1'-biphenyl-2,3,3',4'-tetracarboxylic 2,3:3',4'-dianhydride, naphthalene-1,4,5,8-tetracarboxylic 1,8:4,5-dianhydride, and 1,2,4,5-cyclohexanetetracarboxylic 1,2:4,5-dianhydride.

The amines (1) and (2) for use in the method 2 may be selected from compounds as with the amines for use in the production method 1.

The amine (1) may be used in an amount of typically about 2 to about 4 moles, and preferably 2 to 3 moles, per mole of the carboxylic anhydride. The amine (2) may be used in an amount of typically about 2 to about 4 moles, and preferably 2 to 3 moles, per mole of the carboxylic anhydride.

The carbodiimide is exemplified by the formula:

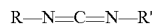

where R and R' are independently selected typically from $C_3$-$C_8$ linear or branched alkyl and 3- to 8-membered cycloalkyl, each of which may have a heteroatom-containing substituent or substituents. R and R' may be identical or different. R and R' may be linked to each other to form a ring with the —N=C=N— group.

Non-limiting examples of the $C_3$-$C_8$ linear or branched alkyl include propyl, isopropyl, butyl, isobutyl, s-butyl, t-butyl, pentyl, isopentyl, s-pentyl, t-pentyl, hexyl, isohexyl, s-hexyl, and t-hexyl.

Non-limiting examples of the 3- to 8-membered cycloalkyl include cyclopropyl, cyclobutyl, cyclopentyl, cyclohexyl, and cyclooctyl.

Non-limiting examples of the heteroatom-containing substituents include nitrogen-containing substituents including amino; and di-($C_1$-$C_3$ alkyl)amino such as dimethylamino.

Non-limiting examples of the carbodiimide include diisopropylcarbodiimide, dicyclohexylcarbodiimide, and N-(3-dimethylaminopropyl)-N'-ethylcarbodiimide. Non-limiting examples of the salt of the carbodiimide include hydrochlorides (such as N-(3-dimethylaminopropyl)-N'-ethylcarbodiimide hydrochloride).

The carbodiimide may be used in an amount of typically about 2 to about 6 moles, and preferably 2 to 4 moles, per mole of the carboxylic anhydride.

The solvent for use herein is preferably selected from proton-acceptor solvents such as pyridine, triethylamine, and tributylamine, each of which has excellent solubility with respect to the amic acid. Each of these solvents may be used alone or in combination as a mixture.

The solvent may be used in an amount of typically about 50 to about 300 weight percent, and preferably 100 to 250 weight percent, relative to the total weight of the amic acid(s). The solvent, when used in an amount greater than the range, tends to cause a lower reaction rate, because of lower concentrations of the reactants.

The reaction is generally performed at normal atmospheric pressure. The reaction atmosphere is not limited, as long as not adversely affecting the reaction, and may be selected from any atmospheres such as air atmosphere, nitrogen atmosphere, and argon atmosphere. The agings (reactions) may be performed at a temperature of typically about 30° C. to about 70° C. The aging between the carboxylic anhydride and the amine may be performed for a time of typically about 0.5 to about 5 hours, and the aging between the amic acid and the amine may be performed for a time of typically about 0.5 to about 20 hours. The reactions may be performed according to any system such as batch system, semi-batch system, or continuous system.

After the completion of the reactions, the resulting reaction product may be separated/purified typically by a separation process such as filtration, concentration, distillation, extraction, crystallization, adsorption, recrystallization, or column chromatography, or a separation process as any combination of them.

The compounds represented by Formula (1) can undergo self-association via hydrogen bonding at amido bond moieties to form fibrous self-assembled structures. The compounds represented by Formula (1), when each mutually dissolved in a fluid organic substance, can thicken and/or gelatinize the fluid organic substance, or can uniformly stabilize a composition containing the fluid organic substance. This is because the $R^2$ group (aliphatic hydrocarbon group containing 1 to 4 carbon atoms) offers strong intermolecular hydrogen bonding actions, and the $R^3$ group (aliphatic hydrocarbon group containing 6 or more carbon atoms) offers affinity for the fluid organic substance. In addition, the compounds, as containing two different types of groups ($R^2$ and $R^3$ groups) in side chains, have weaker interaction among the side chains and less undergo crystallization, compared to containing one type of group. Thus, the compounds have excellent solubility in fluid organic substances and can thicken/stabilize almost any fluid organic substances without limitation. Namely, the compounds have selectivity for a wide variety of target fluid organic substances (fluid organic substances to be thickened). The compounds can thicken/stabilize a fluid organic substance can form a thickened/stabilized composition being stable with time, while maintaining the transparency of the fluid organic substance when the fluid organic substance has transparency. The compounds are therefore useful as thickening/stabilizing agents for fluid organic substances, and, more specifically, are useful as any of thickeners, gelling agents, and stabilizers for the fluid organic substances. In contrast, a compound represented by Formula (1) in which the groups $R^2$ and $R^3$ are identical groups (namely, a compound represented by Formula (1) having four identical groups as side chains); and a compound represented by Formula (1) in which the groups $R^2$ and $R^3$ are different groups, but at least one of the groups $R^2$ and $R^3$ contains carbon atoms in a number out of the range, tend to be crystallized by the interaction among the side chains, are limited in types of fluid organic substances which the compounds can thicken/stabilize, and have narrower selectivity for fluid organic substances to be thickened, thus being undesirable. These compounds, when mutually dissolved in a fluid organic substance, often become cloudy and hardly maintain a beautiful appearance. In addition, these compounds tend to have a decreasing viscosity with time.

Thickening/Stabilizing Agent

The thickening/stabilizing agent according to the present invention includes each of the compounds represented by Formula (1) alone or in combination.

The thickening/stabilizing agent according to the present invention may contain, as needed, one or more other thickening/stabilizing agents than the compounds represented by Formula (1). However, the compound(s) represented by Formula (1) may be present in a content of typically 0.5 weight percent or more, preferably 1 weight percent or more, more preferably 10 weight percent or more, particularly preferably 30 weight percent or more, furthermore preferably 60 weight percent or more, and most preferably 80 weight percent or more, of the total weight (100 weight percent) of the thickening/stabilizing agent according to the present invention. When two or more different compounds represented by Formula (1) are present, the term "content" refers to the total content of them. The upper limit of the content of the compound represented by Formula (1) is 100 weight percent. The compound represented by Formula (1), if present in a content out of the range, tends to less thicken/gelatinize a fluid organic substance, or to less uniformly stabilize a composition containing the fluid organic substance.

As used herein, the term "thickening/stabilizing agent" refers to a compound that is dissolved in a fluid organic substance to develop viscosity. The "thickening/stabilizing agent" is a concept including thickeners, which impart viscosity to the fluid organic substance; gelling agents, which gelatinize the fluid organic substance; and stabilizers, which increase the viscosity of a composition containing the fluid organic substance so as to stabilize the composition uniformly. Non-limiting examples of such other thickening/stabilizing agents include vehicles (bases); hydroxyfatty acids; acrylic polymers; oligomer esters such as dextrin fatty acid esters; and particles typically of metal oxides.

The form of the thickening/stabilizing agent according to the present invention may be selected from various forms such as powders, granules, liquids, and milky lotions.

The thickening/stabilizing agent according to the present invention can thicken and/or gelatinize a fluid organic substance by dissolving the agent mutually in a fluid organic substance (preferably by mixing the agent with the fluid organic substance, heating them to dissolve mutually in each other, and then cooling the resulting mixture). The thickening/stabilizing agent can thicken and/or gelatinize the fluid organic substance to a desired viscosity according to the intended use, at a thickening ratio within the range of from greater than 30 times to 10000 times, and preferably from greater than 30 times to 5000 times.

Thickened/Stabilized Composition

The thickened/stabilized composition according to the present invention includes the thickening/stabilizing agent and a fluid organic substance, in which the fluid organic substance is thickened and/or gelatinized by the thickening/stabilizing agent, or the composition itself is uniformly stabilized by the thickening/stabilizing agent.

The thickened/stabilized composition according to the present invention may be produced typically through the step of dissolving the thickening/stabilizing agent and the fluid organic substance mutually in each other. More specifically, the thickened/stabilized composition may be produced typically by mixing the whole quantity of the fluid organic substance with the thickening/stabilizing agent, heating them to mutually dissolve in each other, and cooling the resulting mixture. The thickened/stabilized composition may also be produced by mixing the thickening/stabilizing agent with part of the fluid organic substance, heating the two components to dissolve mutually in each other, cooling the resulting mixture to give a thickened/stabilized composition, and mixing the thickened/stabilized composition with the remainder of the fluid organic substance.

The fluid organic substance, which is a raw material, is an organic substance having a viscosity of typically less than 0.1 Pa·s, where the viscosity is a viscosity ($\eta$) as determined at 25° C. and a shear rate of 10 (1/s)) using a rheometer. Non-limiting examples of the fluid organic substance include hydrocarbon oils such as hexane, cyclohexane, isododecane, benzene, toluene, poly-α-olefins, and liquid paraffin; ethers such as tetrahydrofuran; halogenated hydrocarbons such as carbon tetrachloride and chlorobenzene; petroleum components such as kerosenes, gasoline, light oils, and heavy oils; animal and vegetable oils such as sunflower oil, olive oil, soybean oil, corn oil, castor oil, beef tallow, jojoba oil, and squalane; silicones including silicone oils such as dimethylpolysiloxanes, methylphenylpolysiloxanes, and decamethylcyclopentasiloxane; esters such as octyldodecyl oleate, cetyl octanoate, cetyl ethylhexanoate, glyceryl triisooctanoate, neopentyl glycol diisooctanoate, and tricaprylin; aromatic carboxylic acids; and pyridine. These substances may be used alone or in combination.

The thickening/stabilizing agent may be mixed (or used) in an amount of typically 0.1 to 100 parts by weight, preferably 0.5 to 90 parts by weight, particularly preferably 1 to 80 parts by weight, and most preferably 1 to 30 parts by weight, per 1000 parts by weight of the fluid organic substance, while the amount may vary depending on the type of the fluid organic substance. The thickening/stabilizing agent, when mixed (or used) in an amount within the range, gives a composition in which the fluid organic substance is thickened and/or gelatinized, or gives a composition having a uniformly stabilized formulation.

The thickened/stabilized composition according to the present invention may further contain a component or components within ranges not adversely affecting the advantageous effects of the present invention, in addition to the thickening/stabilizing agent and the fluid organic substance. Non-limiting examples of such other components include common compounds such as medicinal components, pigments, and flavors, which are to be contained in compositions requiring thickening and/or stabilization and which are used typically as or for cosmetics, coating materials, foodstuffs, and pharmaceutical preparations.

The temperature upon mutual dissolution may be selected as appropriate according to the types of the thickening/stabilizing agent and the fluid organic substance to be used. The temperature is not limited, as long as being such a temperature that the thickening/stabilizing agent and the fluid organic substance are mutually dissolved in each other, but is preferably not higher than 100° C. When the fluid organic substance has a boiling point of 100° C. or lower, the temperature is preferably around the boiling point.

The cooling after mutual dissolution may be performed in any manner, as long as capable of cooling the resulting composition down to 25° C. or lower. The cooling may be performed gradually at room temperature, or may be performed rapidly typically by ice cooling.

The thickened/stabilized composition according to the present invention has a viscosity of typically 0.5 to 10.0 Pa·s, and preferably 1.0 to 8.0 Pa·s, where the viscosity is a viscosity ($\eta$) determined at 25° C. and a shear rate of 10 (1/s) using a rheometer. The viscosity can be adjusted as appropriate according to the intended use, within the range of from greater than 30 time to 10000 times, and preferably from greater than 30 times to 5000 times, as much as the viscosity of the fluid organic substance, which is a raw material.

The thickened/stabilized composition according to the present invention is not limited, as long as being a composition containing a fluid organic substance and being desired to be thickened and/or stabilized. Non-limiting examples of the thickened/stabilized composition include cosmetics, coating materials, foodstuffs, and pharmaceutical preparations.

EXAMPLES

The present invention will be illustrated in further detail with reference to several examples below. It should be noted, however, that the examples are by no means intended to limit the scope of the present invention.

Synthesis Example 1: Synthesis of Thickening/Stabilizing Agent (1) (1,2,4,5-benzenetetracarboxylic Acid di(butyramide) di(oleylamide))

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 7.4 g (0.028 mol) of oleylamine were charged. The components were aged for 3 hours while setting the system internal temperature at 50° C.

Subsequently, 2.1 g (0.028 mol) of butylamine and 7.0 g (0.056 mol) of diisopropylcarbodiimide were charged, followed by aging for further 8 hours to give a crude mixture.

After removing low-boiling components from the crude mixture on an evaporator, the resulting matter was washed with methanol and yielded a pale yellow wet powder. Further, the obtained wet powder was recrystallized from $CHCl_3/CH_3OH$ (70/30 (v/v)) and yielded 7.3 g of 1,2,4,5-benzenetetracarboxylic di(butyramide) di(oleylamide) in a yield of 61%. This was a mixture of 1,2,4,5-benzenetetracarboxylic acid 1,4-di(butyramide)-2,5-di(oleylamide) and 1,2,4,5-benzenetetracarboxylic acid-1,5-di(butyramide)-2,4-di(oleylamide). The reaction product was identified in structure by $^1$H-NMR.

$^1$H-NMR (270 MHz, $CDCl_3$): δ 0.75-1.1 (m, 12H), 1.01-1.86 (m, 64H), 1.96-2.04 (m, 8H), 5.25-5.55 (m, 4H), 8.5-9.5 (m, 2H)

Synthesis Example 2: Synthesis of Thickening/Stabilizing Agent (2) (1,2,4,5-cyclohexanetetracarboxylic Acid di(butyramide) di(oleylamide))

Into a 100-mL four-neck separable flask equipped with a Dimroth condenser, a nitrogen inlet, a dropping funnel, and a thermocouple, 20 mL of pyridine, 4.5 g (0.02 mol) of 1,2,4,5-cyclohexanecarboxylic 1,2:4,5-dianhydride, and 10.7 g (0.04 mol) of oleylamine were charged. The components were aged for 3 hours, while setting the system internal temperature at 50° C.

Subsequently, 2.9 g (0.02 mol) of butylamine and 5.5 g (0.044 mol) of diisopropylcarbodiimide were charged, followed by aging for further 8 hours to give a crude mixture.

After removing low-boiling components from the crude mixture on an evaporator, the resulting matter was washed with methanol and yielded a pale yellow wet powder. Further, the obtained wet powder was recrystallized from $CHCl_3/CH_3OH$ (70/30 (v/v)) and yielded 11.6 g of 1,2,4,5-cyclohexanetetracarboxylic acid di(butyramide) di(oleylamide) in a yield of 67%, as a mixture of 1,2,4,5-cyclohexanetetracarboxylic acid-1,4-di(butyramide)-2,5-di(oleylamide) and 1,2,4,5-cyclohexanetetracarboxylic acid-1,5-di(butyramide)-2,4-di(oleylamide). The reaction product was identified in structure by $^1$H-NMR.

$^1$H-NMR (270 MHz, $CDCl_3$): δ 0.81-0.97 (m, 12H), 0.97-1.61 (m, 64H), 1.82-2.04 (m, 8H), 2.50-3.10 (m, 4H), 3.30-3.45 (m, 4H), 5.25-5.45 (m, 4H), 6.25-6.30 (m, 4H)

Synthesis Example 3: Synthesis of Thickening/Stabilizing Agent (3) (1,2,4,5-benzenetetracarboxylic Acid di(2-ethylhexylamide) di(oleylamide))

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 7.4 g (0.028 mol) of oleylamine were charged. The components were aged for 3 hours while setting the system internal temperature at 50° C.

Subsequently, 3.6 g (0.028 mol) of 2-ethylhexylamine and 7.0 g (0.056 mol) of diisopropylcarbodiimide were charged, followed by aging for further 8 hours to give a crude mixture.

After removing low-boiling components from the crude mixture on an evaporator, the resulting matter was washed with methanol and yielded a pale yellow wet powder. The obtained wet powder was recrystallized from $CHCl_3/CH_3OH$ (70/30 (v/v)) and yielded 5.9 g of 1,2,4,5-benzenetetracarboxylic acid di(2-ethylhexylamide) di(oleylamide) in a yield of 51%. This was a mixture of 1,2,4,5-benzenetetracarboxylic acid-1,4-di(2-ethylhexylamide)-2,5-di(oleylamide) and 1,2,4,5-benzenetetracarboxylic acid-1,5-di(2-ethylhexylamide)-2,4-di(oleylamide). The reaction product was identified in structure by $^1$H-NMR.

$^1$H-NMR (270 MHz, $CDCl_3$): δ 0.81-1.02 (m, 18H), 1.03-1.85 (m, 74H), 1.96-2.04 (m, 8H), 5.35-5.56 (m, 4H), 8.5-9.5 (m, 2H)

Synthesis Example 4: Synthesis of Thickening/Stabilizing Agent (4) (1,2,4,5-benzenetetracarboxylic Acid di(hexylamide) di(oleylamide))

Into a 100-mL four-neck separable flask equipped with a Dimroth condenser, a nitrogen inlet, a dropping funnel, and a thermocouple, 20 mL of pyridine, 3.0 g (0.014 mol) of 1,2,4,5-benzenetetracarboxylic 1,2:4,5-dianhydride, and 7.4 g (0.028 mol) of oleylamine were charged. The components were aged for 3 hours while setting the system internal temperature at 50° C.

Subsequently, 2.8 g (0.028 mol) of hexylamine and 7.0 g (0.056 mol) of diisopropylcarbodiimide were charged, followed by aging for further 8 hours to give a crude mixture.

After removing low-boiling components from the crude mixture on an evaporator, the resulting matter was washed with methanol and yielded a pale yellow wet powder. The obtained wet powder was recrystallized from $CHCl_3/CH_3OH$ (70/30 (v/v)) and yielded 8.1 g of 1,2,4,5-benzenetetracarboxylic acid di(hexylamide) di(oleylamide) in a yield of 64%. This was a mixture of 1,2,4,5-benzenetetracarboxylic acid-1,4-di(hexylamide)-2,5-di(oleylamide) and 1,2,4,5-benzenetetracarboxylic acid-1,5-di(hexylamide)-2,4-di(oleylamide). The reaction product was identified in structure by $^1$H-NMR.

$^1$H-NMR (270 MHz, $CDCl_3$): δ 0.80-1.01 (m, 12H), 1.0-1.82 (m, 72H), 1.96-2.04 (m, 8H), 5.31-5.61 (m, 4H), 8.5-9.5 (m, 2H)

Example 1

Fluid organic substances used herein were liquid paraffin (viscosity: 0.14 Pa·s), isododecane (viscosity: 0.001 Pa·s), cetyl octanoate (viscosity: 0.012 Pa·s), and tricaprylin (viscosity: 0.023 Pa·s), each having a boiling point of 100° C. or higher, as presented in the table. One cubic centimeter (1 $cm^3$) each of the fluid organic substances was measured and independently placed in test tubes, each combined with 10 mg of the thickening/stabilizing agent (1) prepared in the synthesis example, stirred with heating at 100° C. to dissolve the fluid organic substance and the thickening/stabilizing agent (1) mutually in each other, cooled down to 25° C., and yielded a series of thickened/stabilized compositions.

The resulting thickened/stabilized compositions had viscosities as follows:

Liquid paraffin thickened/stabilized composition: 4.84 Pa·s

Isododecane thickened/stabilized composition: 1.98 Pa·s

Cetyl octanoate thickened/stabilized composition: 2.48 Pa·s

Tricaprylin thickened/stabilized composition: 7.87 Pa·s

A thickening ratio was determined according to the expression below, and the thickening effect was evaluated according to criteria below. Samples rated as 5 or more on all the fluid organic substances were evaluated as having good thickening effect (Good), and the other samples were evaluated as having poor thickening effect (Poor).

Thickening ratio=(Viscosity of thickened/stabilized composition)/(Viscosity of fluid organic substance before thickening/stabilization)

Evaluation Criteria

1: 2.0 times or less;
2: from greater than 2.0 time to 4.8 times;
3: from greater than 4.8 times to 10 times;
4: from greater than 10 times to 30 times;
5: from greater than 30 times to 200 times;
6: from greater than 200 times to 500 times;
7: from greater than 500 times to 3000 times;
8: greater than 3000 times The viscosities of the fluid organic substances before thickening/stabilization and of the thickened/stabilized compositions were determined each in the following manner. The measurement was performed using a viscosity/viscoelastometer (rheometer) (HAAKE RheoStress 600 (trade name)) equipped with a cone-and-plate sensor and a Peltier temperature controller. The cone-and-plate system in the sensor used had a diameter of 60 mm with a cone angle of 1°, or a diameter of 35 mm with a cone angle of 1°, 2°, or 4°. The viscosities were measured in a steady flow viscosity measurement mode at 25° C. and different shear rates varying in a log scale from 0.001 to 100 (1/s), on the basis of which a viscosity curve was plotted. A viscosity at a shear rate of 10 (1/s) was determined from the viscosity curve, and this was defined as the viscosity in the present invention. Each plot employed values obtained at the time point when the torque value variation of the instrument was settled within the range of 5% and the data became stable.

Example 2 and Comparative Examples 1 and 2

Procedures similar to that in Example 1 were performed, except for using the thickening/stabilizing agents given in the table, instead of the thickening/stabilizing agent (1).

The results are collectively presented in the following table.

The thickening/stabilizing agents according to the present invention can offer excellent thickening effects on a wider variety of fluid organic substances as compared with the thickening/stabilizing agents according to the comparative examples. Namely, the thickening/stabilizing agents according to the present invention have wider selectivities for fluid organic substances to be thickened.

INDUSTRIAL APPLICABILITY

The compounds represented by Formula (1) according to the present invention, when dissolved mutually in a fluid organic substance, can readily thicken and/or gelatinize the fluid organic substance, or can stabilize a composition containing the fluid organic substance uniformly. In addition, the compounds can maintain the thickened and/or gelatinized state stably. Thus, the compounds represented by Formula (1) according to the present invention are advantageously usable as thickening/stabilizing agents typically for cosmetics, coating materials, foodstuffs, and pharmaceutical preparations.

The invention claimed is:

1. A compound represented by Formula (1):

$$(R^2-HNOC)_{4-n}-R^1-(CONH-R^3)_n \quad (1)$$

wherein $R^1$ is a group resulting from removing four hydrogen atoms from a structural formula of an aromatic hydrocarbon or cyclohexane;

$R^2$ is, independently in each occurrence, an aliphatic hydrocarbon group containing 1 to 4 carbon atoms;

$R^3$ is, independently in each occurrence, an aliphatic hydrocarbon group containing 6 or more carbon atoms; and n is an integer of 1 to 3.

2. The compound according to claim 1, wherein the aromatic hydrocarbon in $R^1$ is selected from benzene, benzophenone, biphenyl, and naphthalene.

3. The compound according to claim 1, wherein $R^1$ is a group resulting from removing four hydrogen atoms from a structural formula of one of benzene and cyclohexane.

4. A thickening/stabilizing agent comprising the compound according to any one of claims 1 to 3.

5. A thickened/stabilized composition comprising:

the thickening/stabilizing agent according to claim 4; and a fluid organic substance.

TABLE 1

|  |  | Example 1 Thickening/ stabilizing agent (1) | Example 2 Thickening/ stabilizing agent (2) | Comparative Example 1 Thickening/ stabilizing agent (3) | Comparative Example 2 Thickening/ stabilizing agent (4) |
|---|---|---|---|---|---|
| Fluid organic substance | Liquid paraffin | 5 | 5 | 4 | 4 |
|  | Isododecane | 7 | 8 | 6 | 6 |
|  | Cetyl octanoate | 6 | 6 | 6 | 5 |
|  | Tricaprylin | 6 | 6 | 3 | 5 |
|  | Thickening effect | Good | Good | Poor | Poor |

6. A method for producing a thickened/stabilized composition, the method comprising the step of
mutually dissolving the thickening/stabilizing agent according to claim 4 and a fluid organic substance in each other.

* * * * *